United States Patent
Guo et al.

(10) Patent No.: US 9,546,143 B2
(45) Date of Patent: Jan. 17, 2017

(54) METHOD FOR PREPARING HIGH-QUALITY EPOXIDIZED FATTY ACID ESTER WITH MICRO-REACTION DEVICE

(71) Applicant: NANJING TECH UNIVERSITY (CN), Nanjing (CN)

(72) Inventors: Kai Guo, Nanjing (CN); Zheng Fang, Nanjing (CN); Xin Li, Nanjing (CN); Ning Zhu, Nanjing (CN); Li Wan, Nanjing (CN); Wei He, Nanjing (CN); Kai Zhang, Nanjing (CN); Pingkai Ouyang, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 0 days.

(21) Appl. No.: 15/201,274

(22) Filed: Jul. 1, 2016

(65) Prior Publication Data
US 2016/0311789 A1    Oct. 27, 2016

(30) Foreign Application Priority Data
Apr. 7, 2016 (CN) .......................... 2016 1 0214872

(51) Int. Cl.
C07D 301/18 (2006.01)
C07D 301/16 (2006.01)
B01J 19/00 (2006.01)

(52) U.S. Cl.
CPC .......... *C07D 301/16* (2013.01); *B01J 19/0093* (2013.01); *B01J 2219/00795* (2013.01); *B01J 2219/00873* (2013.01); *B01J 2219/00889* (2013.01); *B01J 2219/00905* (2013.01)

(58) Field of Classification Search
CPC ................. C07D 301/16; B01J 19/0093; B01J 2219/00905; B01J 2219/00873; B01J 2219/00889
USPC ....................................................... 549/527
See application file for complete search history.

(56) References Cited

FOREIGN PATENT DOCUMENTS

| CN | 102876462 A | * | 1/2013 |
|----|-------------|---|--------|
| CN | 102993133   | * | 3/2013 |

* cited by examiner

*Primary Examiner* — T. Victor Oh
(74) *Attorney, Agent, or Firm* — CBM Patent Consulting, LLC

(57) ABSTRACT

A method for preparing a high-quality epoxidized fatty acid ester with a micro-reaction device, including: respectively pumping an aqueous hydrogen peroxide solution and a carboxylic acid at the same time into a first micro-mixer; after the reaction in the first micro-reactor, respectively pumping the output material and an unsaturated fatty acid ester into a second micro-mixer;
completely mixing them and then introducing the mixture into a second micro-reactor; and after a complete reaction, water-rinsing the organic phase part of the resultant reaction liquid and drying the same to obtain the epoxidized fatty acid ester.

9 Claims, 1 Drawing Sheet

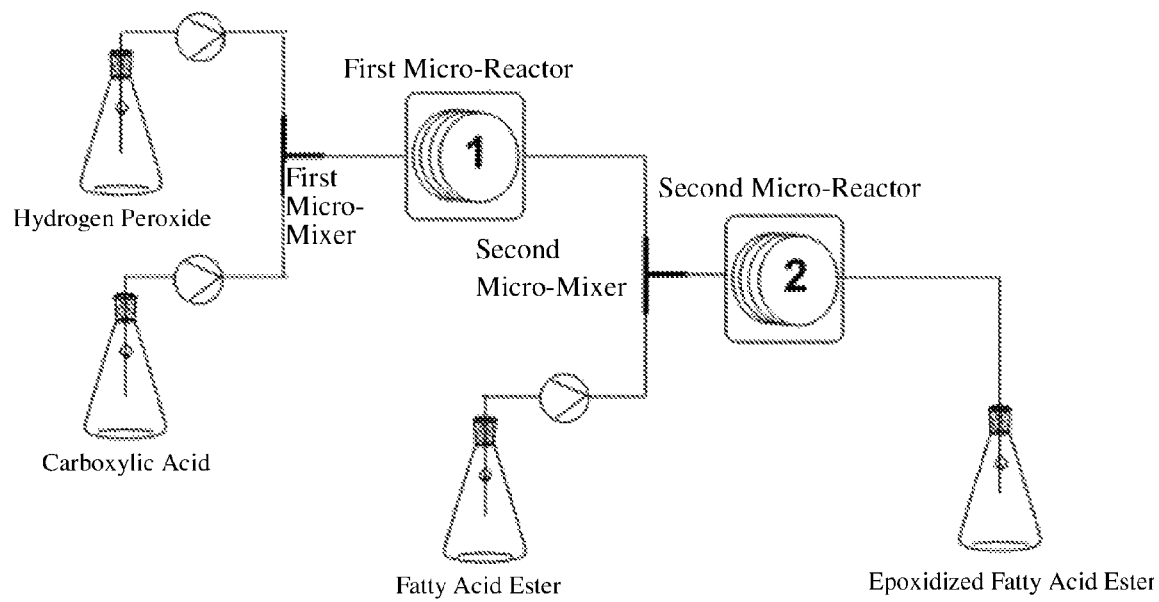

METHOD FOR PREPARING HIGH-QUALITY EPOXIDIZED FATTY ACID ESTER WITH MICRO-REACTION DEVICE

This application claims priority to Chinese Patent Application Ser. No. CN201610214872.7 filed 7 Apr. 2016.

FIELD OF THE INVENTION

The present invention pertains to the field of chemical industry, and particularly relates to a method for preparing high-quality epoxidized fatty acid ester with a micro-reaction device.

BACKGROUND OF THE INVENTION

As the plastic article is increasingly widely applied, a plasticizer product is introduced into many industries of national economy, especially for the application thereof in industries of food, medicine, toys, hygienic products and the like directly related to human health, which brings about higher health and safety requirements to the plasticizer industry. Detoxifying of the plasticizer industry has become a major livelihood issue concerned by the public, and transformation and upgrading of industry from the petrochemical plasticizer to a biological and non-toxic plasticizer have become imperative. In European countries, American, Japan and South Korea and the like, the traditional petrochemical plasticizer has been prohibited in many industries by office order, and instead related green and nontoxic plasticizer species such as citrates, dihydroxy alcohol esters and epoxidized plant oils are used. The European Union provided temporary regulations in 1999 to limit the application of the phthalate plasticizer in children's toys, and after multiple revisions the new European Toy Safety Directive (No. EC765/2008) was officially put into implementation by the European Union in 2011, which expressly stipulated that no petrochemical phthalate plasticizer should be added into toys and other articles for children; the REACH regulations promulgated by the European Union in 2007 explicitly prohibited the application of the phthalate plasticizer in industries closely related to human health; and in early 1990s, the U.S. Environmental Protection Agency (USEPA) had already limited the application of many kinds of phthalate plasticizers in industry fields with high requirements to environment protection and hygiene, such as medical plastic articles, food packages, children's toys and the like; in 2008, President Bush officially signed the CPSIA Act to explicitly limit the application of 6 kinds of phthalate plasticizers in fields of food packages, children's toys, and medicine; and Australia, Japan, South Korea, Argentina and the like have successively promulgated multiple restrictive orders for the application of phthalate plasticizers.

A petrochemical phthalate plasticizer is dominated in the plasticizers produced in China (over 80% market shares). However, the phthalate material is an environmental hormone, which has relatively strong reproductive toxicity and certain carcinogenicity. In China, various health and safety problems have been induced by excessive and improper use of the traditional petrochemical plasticizer. For example, in 2005, the safety problem of fresh-keeping film occurred in Japan induced great attention of Chinese people to safety of plasticizers; in 2008, the European Union promulgated import restriction to toys from China; in 2011, the plasticizer scandal happened in Taiwan; in 2012, the plasticizer crisis of white spirit occurred in China; etc. With ever-increasing pressure of petrochemical resources and improvement of the living standard of people, a variety of problems caused by the plasticizer gain broad attention from people, and related laws and regulations are being perfected day by day; the "Hygienic Standard for Cosmetics" promulgated in 2007 added 3 kinds of phthalate plasticizers into the prohibited group; the Hygienic Standards for Uses of Additives in Food Containers and Packaging Materials promulgated in 2008 limited the application of 7 kinds of phthalate plasticizers; and in 2011, the Ministry of Health in China added phthalate substances into the list of illegal additives in food.

With respect to catalyzing technology, the catalyzing technology of relevant foreign production enterprises still is still highly confidential, while Chinese enterprises still use in production sulfuric acid as the main catalyst, which causes serious pollution and poor product quality, showing a significant disparity from the foreign catalyzing technology. New catalysts such as sulfonic acids, solid superacids, heteropoly acids have been developed in scientific researches, and there are some researches related to enzyme catalyzing technology. These enzymes have overcome the disadvantages of strong corrosivity, many side reactions, unmanageable reaction waste liquids of traditional concentrated sulphuric acids, but there are still disadvantages of high cost, harsh reaction conditions, high power consumption and raw material consumption, complex post-processing, poor product quality and the like in different degrees, which greatly blocks the industrialized application of the catalyst. With respect to engineering technology, Chinese enterprises still mainly use the batch production process, and the relevant enterprises are of small scales, and have unstable production, high power consumption and high discharge, which greatly blocks large-scale industry development and the relevant application of biological plasticizers.

CN1204970C discloses a reaction-controlled phase transfer catalyst used for oxidation and an oxidation process for catalyzing epoxidation of a double bond by using the specifically designed catalyst, wherein the catalysts of said catalyzing system can react in the presence of hydrogen peroxide to obtain an active substance dissolved in the reaction system, thereby catalyzing the epoxidation reaction; however, when the hydrogen peroxide is completely consumed, the catalyst is reverted to the original structure and thus precipitated out, thereby realizing recycling of the catalyst. Currently, said catalyst system has been successfully used in preparation of propylene epoxide and epoxy cyclohexane. However, there are a series of problems of said catalyst system, such as the need of using a large amount of organic solutions, which causes that the successive processing is complex and consumes power. CN102875492 A provides a novel method for preparing an epoxidized fatty acid ester from an unsaturated fatty acid ester. The epoxidized fatty acid ester is generated by epoxidizing the unsaturated fatty acid ester using a metal-substituted polyoxometalate compound as the catalyst and using hydrogen peroxide as the oxygen source in the presence of neither other organic solvents nor organic peroxy acids. However, this method needs to prepare metal-substituted polyoxometalate as the catalyst, and thus is complex in the process. CN102876462 B discloses a method for preparing high-quality epoxidized soybean oil, including mixing an aqueous hydrogen peroxide solution with an aqueous formic acid solution; then adding a catalyst and a stabilizer; pumping soybean oil and the aforementioned mixture into a micro-channel modularization reaction device and maintaining a reaction residence time of 2-12 min; reacting at 65-95° C.; introducing the reaction products into a separator, adding an aqueous NaCO3 solution and standing for layering; removing the lower aqueous solution and water rinsing the upper organic phase; and removing the moisture via rotary evaporation so as to obtain the high-quality epoxidized soybean oil. However, this method needs the addition of a stabilizer and has a high raw material cost; meanwhile, it also needs the addition of sulfuric acid as a catalyst, which results in the occurrence of a ring-opening reaction as a side reaction and the increase of three wastes. CN 102993133 B discloses a method for preparing an epoxidized fatty acid methyl ester with a micro-reactor in one step, wherein the addition of a stabilizer and the addition of sulfuric acid as a catalyst are also involved, and thus it may cause ring opening of an epoxy group, reduction of the epoxy value of the epoxy group, and inevitable increase of the three wastes.

CN104560407 A discloses a novel method for preparing an epoxy plasticizer, including mixing a highly-concentrated hydrogen peroxide and a highly-concentrated formic acid at room temperature to obtain a highly-concentrated peroxy-formic acid mixture; then feeding soybean oil into the reaction equipment in one time to start an exothermic self-initiated reaction until the temperature is 60-70° C.; then reacting at a controlled reaction temperature of 70-90° C. for 3-4 hours; performing centrifugal separation to remove the aqueous phase; and dehydrating the crude oil phase, wherein the epoxy value of the resultant epoxidized fatty acid ester may up to over 7.0. This invention avoids the use of sulfuric acid as the catalyst, and thus avoids the large amount of three wastes. However, there are significant potential safety hazards in the early production of the highly-concentrated peroxyformic acid mixture and the safety level of the process flow is low, which easily causes an exploration.

SUMMARY OF THE INVENTION

The technical problem to be solved by the present invention is to provide a method for preparing a high-quality epoxidized fatty acid ester with a micro-reaction device, so as to solve the problems in the prior art such as inaccurate temperature control, low selectivity, low safety level, slow epoxidation rate, discontinuous production and the need of preparing a new catalyst.

In order to solve the aforementioned technical problem, the present invention adopts a technical solution as follows:

A method for preparing a high-quality epoxidized fatty acid ester with a micro-reaction device, including the following steps:

(1) respectively pumping an aqueous hydrogen peroxide solution and a carboxylic acid at the same time into a first micro-mixer of the micro-reaction device, completely mixing them and then introducing the mixture into a first micro-reactor of the micro-reaction device to react; and (2) respectively pumping the output material of the first micro-reactor and an unsaturated fatty acid ester at the same time into a second micro-mixer of the micro-reaction device, completely mixing them and then introducing the mixture into a second micro-reactor of the micro-reaction device to react completely, water rinsing the organic phase part of the resultant reaction liquid and drying to obtain the epoxidized fatty acid ester.

In step (1), the mass fraction of the solute, hydrogen peroxide, included in the aqueous hydrogen peroxide solution is 50-70%.

In step (1), the carboxylic acid may be formic acid, acetic acid, propanoic acid or butyric acid.

In step (1), the molar ratio of hydrogen peroxide to carboxylic acid is 1:1-5, preferably 1:1-4.

In step (1), in the first micro-reactor, the reaction temperature is 35-85° C., preferably 40-60° C.; and the residence time is 1-8 min, preferably 2-6 min.

In step (2), the unsaturated fatty acid ester is an unsaturated fatty acid methyl ester, an unsaturated fatty acid ethyl ester, an unsaturated fatty acid propyl ester or an unsaturated fatty acid butyl ester, which is prepared by respectively transesterifying the soybean oil with methanol, ethanol, propanol or butanol.

In step (2), in the second micro-reactor, the reaction temperature is 65-115° C., preferably 75-105° C.; and the residence time is 4-8 min, preferably 5-7 min.

In step (2), water rinsing refers to rinsing the organic phase with water until the pH is 6.5-7.5, and the drying method adopts anhydrous sodium sulfate, anhydrous magnesium sulfate or the like to perform drying.

The molar ratio of hydrogen peroxide to double bonds of unsaturated fatty acid ester is 5-20:1, preferably 8-16:1.

The micro-reaction device includes the first micro-mixer, the first micro-reactor, the second micro-mixer and the second micro-reactor sequentially connected in series via connecting tubes, wherein the feed inlet of the first micro-mixer is connected to a first liquor inlet and a second liquor inlet respectively, and the feed inlet of the second micro-mixer is connected to the outlet of the first micro-reactor and a third liquor inlet respectively.

The model of the first and second micro-mixers is slit plate mixer LH25(Hastelloy C), and the model of the first and second micro-reactors is sandwich reactor HC.

Beneficial Effect:

As compared with the prior art, the preparation method of the present invention is simple and effective, and has advantages of high selectivity, high safety level, continuous production and no need of new catalysts. Meanwhile, the epoxidized fatty acid ester prepared by the method of the present invention has a high epoxy degree.

DESCRIPTION OF THE DRAWING

FIG. 1 is a schematic flow chart of the reaction of the present invention.

DETAILED DESCRIPTION OF THE EMBODIMENTS

The present invention can be better understood in accordance with the following embodiments. However, those skilled in the art will readily understand that the contents described by the embodiments are only intended to illustrate the present invention, rather than limiting the present invention described in details in the claims.

In the following embodiments, the used micro-reaction device is as shown in FIG. 1; a first liquor inlet and a second liquor inlet are respectively connected to a first micro-mixer via a tube; the first micro-mixer is connected in series with a first micro-reactor via a tube; the outlet of the first micro-reactor and a third liquor inlet are respectively connected to a second micro-mixer via a tube; the second micro-mixer is connected in series with a second micro-reactor and a product collecting bottle respectively via a tube; and the input and output of reaction raw-materials and products are achieved by means of an accurate pump.

The model of the first and second micro-mixers is slit plate mixer LH25(Hastelloy C), and the model of the first and second micro-reactors is sandwich reactor HC.

The concentration of the hydrogen peroxide used in the following embodiments is a mass percent concentration, and the unsaturated fatty acid methyl ester, the unsaturated fatty acid ethyl ester, the unsaturated fatty acid propyl ester or the unsaturated fatty acid butyl ester is prepared by respectively transesterifying the soybean oil with methanol, ethanol, propanol or butanol.

Embodiment 1

Into the first micro-mixer of the micro-reaction device are pumped hydrogen peroxide (50 wt %) and formic acid in a molar ratio of 1:1 respectively at the same time via the first liquor inlet and the second liquor inlet. They are completely mixed and then introduced into the first micro-reactor of the micro-reaction device, and retained at 40° C. for 2 min. Then the output material and an unsaturated fatty acid methyl ester are respectively pumped at the same time into the second micro-mixer of the micro-reaction device, completely stirred, then introduced into the second micro-reactor of the micro-reaction device, and retained at 75° C. for 5 min. The output material of the second micro-reactor is introduced into a separator and stands for layering. The lower aqueous solution is removed, and the upper organic phase is water-rinsed until the pH is 6.5-7.5 and then dried with an anhydrous sodium sulfate to obtain an epoxidized fatty acid ester with an epoxy value of 4.5%.

Embodiment 2

Into the first micro-mixer and the first micro-reactor are pumped hydrogen peroxide (50 wt %) and formic acid in a molar ratio of 1:4 respectively. They are retained at 60° C. for 6 min. Then the unsaturated fatty acid methyl ester and the output material of the first micro-reactor are pumped into the second micro-mixer and the second micro-reactor with a controlled molar ratio of the hydrogen peroxide to double bonds of the unsaturated fatty acid methyl ester of 16:1, and retained at 105° C. for 7 min. The output material of the micro-reactor is introduced into the separator and stands for layering. The lower aqueous solution is removed, and the upper organic phase is water-rinsed until the pH is 6.5-7.5 and then dried to obtain an epoxidized fatty acid ester with an epoxy value of 6.0%.

Embodiment 3

Into the first micro-mixer and the first micro-reactor are pumped hydrogen peroxide (50 wt %) and acetic acid in a molar ratio of 1:4 respectively. They are retained at 60° C. for 6 min. Then the unsaturated fatty acid methyl ester and the output material of the first micro-reactor are pumped into the second micro-mixer and the second micro-reactor with a controlled molar ratio of the hydrogen peroxide to double bonds of the unsaturated fatty acid methyl ester of 16:1, and retained at 105° C. for 7 min. The output material of the micro-reactor is introduced into the separator and stands for layering. The lower aqueous solution is removed, and the upper organic phase is water-rinsed until the pH is 6.5-7.5 and then dried to obtain an epoxidized fatty acid ester with an epoxy value of 5.5%.

Embodiment 4

Into the first micro-mixer and the first micro-reactor are pumped hydrogen peroxide (50 wt %) and propionic acid in a molar ratio of 1:4 respectively. They are retained at 60° C. for 6 min. Then the unsaturated fatty acid methyl ester and the output material of the first micro-reactor are pumped into the second micro-mixer and the second micro-reactor with a controlled molar ratio of the hydrogen peroxide to double bonds of the unsaturated fatty acid methyl ester of 16:1, and retained at 105° C. for 7 min. The output material of the micro-reactor is introduced into the separator and stands for layering. The lower aqueous solution is removed, and the upper organic phase is water-rinsed until the pH is 6.5-7.5 and then dried to obtain an epoxidized fatty acid ester with an epoxy value of 5.0%.

Embodiment 5

Into the first micro-mixer and the first micro-reactor are pumped hydrogen peroxide (50 wt %) and butyric acid in a molar ratio of 1:4 respectively. They are retained at 60° C. for 6 min. Then the unsaturated fatty acid methyl ester and the output material of the first micro-reactor are pumped into the second micro-mixer and the second micro-reactor with a controlled molar ratio of the hydrogen peroxide to double bonds of the unsaturated fatty acid methyl ester of 16:1, and retained at 105° C. for 7 min. The output material of the micro-reactor is introduced into the separator and stands for layering. The lower aqueous solution is removed, and the upper organic phase is water-rinsed until the pH is 6.5-7.5 and then dried to obtain an epoxidized fatty acid ester with an epoxy value of 4.5%.

Embodiment 6

Into the first micro-mixer and the first micro-reactor are pumped hydrogen peroxide (50 wt %) and formic acid in a molar ratio of 1:4 respectively. They are retained at 60° C. for 6 min. Then the unsaturated fatty acid ethyl ester and the output material of the first micro-reactor are pumped into the second micro-mixer and the second micro-reactor with a controlled molar ratio of the hydrogen peroxide to double bonds of the unsaturated fatty acid ethyl ester of 16:1, and retained at 105° C. for 7 min. The output material of the micro-reactor is introduced into the separator and stands for layering. The lower aqueous solution is removed, and the upper organic phase is water-rinsed until the pH is 6.5-7.5 and then dried to obtain an epoxidized fatty acid ester with an epoxy value of 5.8%.

Embodiment 7

Into the first micro-mixer and the first micro-reactor are pumped hydrogen peroxide (50 wt %) and formic acid in a molar ratio of 1:4 respectively. They are retained at 60° C. for 6 min. Then the unsaturated fatty acid propyl ester and the output material of the first micro-reactor are pumped into the second micro-mixer and the second micro-reactor with a controlled molar ratio of the hydrogen peroxide to double bonds of the unsaturated fatty acid propyl ester of 16:1, and retained at 105° C. for 7 min. The output material of the micro-reactor is introduced into the separator and stands for layering. The lower aqueous solution is removed, and the upper organic phase is water-rinsed until the pH is 6.5-7.5 and then dried to obtain an epoxidized fatty acid ester with an epoxy value of 5.7%.

Embodiment 8

Into the first micro-mixer and the first micro-reactor are pumped hydrogen peroxide (50 wt %) and formic acid in a molar ratio of 1:4 respectively. They are retained at 60° C. for 6 min. Then the unsaturated fatty acid butyl ester and the output material of the first micro-reactor are pumped into the second micro-mixer and the second micro-reactor with a controlled molar ratio of the hydrogen peroxide to double bonds of the unsaturated fatty acid butyl ester of 16:1, and retained at 105° C. for 7 min. The output material of the micro-reactor is introduced into the separator and stands for layering. The lower aqueous solution is removed, and the upper organic phase is water-rinsed until the pH is 6.5-7.5 and then dried to obtain an epoxidized fatty acid ester with an epoxy value of 5.6%.

Embodiment 9

Into the first micro-mixer and the first micro-reactor are pumped hydrogen peroxide (70 wt %) and formic acid in a molar ratio of 1:1 respectively. They are retained at 40° C. for 2 min. Then the unsaturated fatty acid methyl ester and the output material of the first micro-reactor are pumped into the second micro-mixer and the second micro-reactor with a controlled molar ratio of the hydrogen peroxide to double bonds of the unsaturated fatty acid methyl ester of 8:1, and retained at 75° C. for 5 min. The output material of the micro-reactor is introduced into the separator and stands for layering. The lower aqueous solution is removed, and the upper organic phase is water-rinsed until the pH is 6.5-7.5 and then dried to obtain an epoxidized fatty acid ester with an epoxy value of 6.2%.

Embodiment 10

Into the first micro-mixer and the first micro-reactor are pumped hydrogen peroxide (60 wt %) and formic acid in a molar ratio of 1:1 respectively. They are retained at 40° C. for 2 min. Then the unsaturated fatty acid methyl ester and the output material of the first micro-reactor are pumped into the second micro-mixer and the second micro-reactor with a controlled molar ratio of the hydrogen peroxide to double bonds of the unsaturated fatty acid methyl ester of 8:1, and retained at 75° C. for 5 min. The output material of the micro-reactor is introduced into the separator and stands for layering. The lower aqueous solution is removed, and the upper organic phase is water-rinsed until the pH is 6.5-7.5 and then dried to obtain an epoxidized fatty acid ester with an epoxy value of 6.0%.

What is claimed is:

1. A method for preparing a high-quality epoxidized fatty acid ester with a micro-reaction device, comprising the following steps:

(1) respectively pumping an aqueous hydrogen peroxide solution and a carboxylic acid at the same time into a first micro-mixer of the micro-reaction device, completely mixing them and then introducing the mixture into a first micro-reactor of the micro-reaction device to react; and (2) respectively pumping the output material of the first micro-reactor and an unsaturated fatty acid ester at the same time into a second micro-mixer of the micro-reaction device, completely mixing them and then introducing the mixture into a second micro-reactor of the micro-reaction device to react completely, water-rinsing the organic phase part of the resultant reaction liquid and drying to obtain the epoxidized fatty acid ester.

2. The method of claim 1, wherein in step (1), the mass fraction of the solute, hydrogen peroxide, comprised in the aqueous hydrogen peroxide solution is 50-70%.

3. The method of claim 1, wherein in step (1), the carboxylic acid is formic acid, acetic acid, propanoic acid or butyric acid.

4. The method of claim 1, wherein in step (1), the molar ratio of hydrogen peroxide to carboxylic acid is 1:1-5.

5. The method of claim 1, wherein in step (1), in the first micro-reactor the reaction temperature is 35-85° C. and the residence time is 1-8 min.

6. The method of claim 1, wherein in step (2), the unsaturated fatty acid ester is an unsaturated fatty acid methyl ester, an unsaturated fatty acid ethyl ester, an unsaturated fatty acid propyl ester or an unsaturated fatty acid butyl ester.

7. The method of claim 1, wherein in step (2), in the second micro-reactor the reaction temperature is 65-115° C. and the residence time is 4-8 min.

8. The method of claim 1, wherein the molar ratio of hydrogen peroxide to double bonds of the unsaturated fatty acid ester is 5-20:1.

9. The method of claim 1, wherein the micro-reaction device comprises the first micro-mixer, the first micro-reactor, the second micro-mixer and the second micro-reactor sequentially connected in series via connecting tubes, wherein the feed inlet of the first micro-mixer is connected to a first liquor inlet and a second liquor inlet respectively, and the feed inlet of the second micro-mixer is connected to the outlet of the first micro-reactor and a third liquor inlet respectively.

* * * * *